United States Patent [19]
Goldenberg

[11] Patent Number: 6,039,050
[45] Date of Patent: Mar. 21, 2000

[54] DISPOSABLE TOOTHBRUSH AND FLOSSING DEVICE

[76] Inventor: Eugene Goldenberg, Two Kile Ct., Monsey, N.Y. 10952

[21] Appl. No.: 09/362,461

[22] Filed: Jul. 28, 1999

[51] Int. Cl.[7] .................................................. A45D 44/18
[52] U.S. Cl. .......................................... 132/309; 15/167.1
[58] Field of Search ................................... 132/308, 309; 15/167.1

[56] References Cited

U.S. PATENT DOCUMENTS

| | | | |
|---|---|---|---|
| 1,475,789 | 11/1923 | Buckley | 132/309 |
| 3,879,139 | 4/1975 | Dahl et al. | 15/167.1 |
| 5,184,719 | 2/1993 | Gordon | 132/309 |
| 5,369,831 | 12/1994 | Bock | 15/167.1 |
| 5,471,701 | 12/1995 | Parfenie | 15/167.1 |
| 5,528,786 | 6/1996 | Porat et al. | 15/167.1 |
| 5,555,590 | 9/1996 | Blum et al. | 15/167.1 |
| 5,581,838 | 12/1996 | Rocco | 132/309 |
| 5,737,792 | 4/1998 | Quigless | 15/167.1 |
| 5,934,295 | 8/1999 | Gekhter et al. | 132/309 |

*Primary Examiner*—Todd E. Manahan
*Attorney, Agent, or Firm*—Collard & Roe, PC

[57] ABSTRACT

A toothbrush comprised of a handle having a first section, a second section connected to and angled up from the first section, and a third section having a decreased width and thickness from the second section. The third section has a lip on its free end. The first section includes a device for mounting a length of dental floss thereon. The head of the toothbrush consists of a base with a substantially rectangular cross section which has an open end and a closed end. A ridge is located along the top or bottom inside face of the base. The base has a cavity which has a substantially rectangular cross section and contains toothpaste. Attached to the top of the base is a middle plate which extends beyond the base past a bottom end of the base. At the bottom end of the middle plate is a thumbstop attached to the top face of the middle plate at the first end. Attached to a top face of the middle plate is a bristle plate which contains bristles. In addition, a bore hole extends through the bristle plate, through the middle plate to the base. This toothbrush is designed so that the handle can be inserted into the base to assemble the toothbrush, and when desired, pushed further into the base to cause toothpaste lodged in the cavity of the handle to be ejected from the cavity, through the middle plate, through the bristle plate and onto the bristles.

12 Claims, 4 Drawing Sheets

DISPOSABLE TOOTHBRUSH AND FLOSSING DEVICE

BACKGROUND OF THE INVENTION

1. Field of the Invention

The invention relates to a disposable toothbrush which comprises an unattached handle and a head. The handle is angled to allow greater access to teeth. The head has a hollow cavity for storing toothpaste. The handle can be inserted into the head to assemble the toothbrush. Pushing the handle farther into the head causes toothpaste to be ejected from the head and onto bristles of the brush. A user can then brush his teeth and dispose of the toothbrush.

2. The Prior Art

Various disposable toothbrushes have been in use for many years. These brushes typically utilize a two-piece apparatus comprising a hollow head and handle. The head has a set of bristles for brushing the teeth, and has a small amount of toothpaste stored within it.

To use the toothbrush, the handle is inserted into the head, which pushes the toothpaste out of the hollow space in the head and through a hole in the bristle area. The toothbrush is then assembled and toothpaste is already applied to the bristles. Examples of such toothbrushes can be seen in UK Patent Application No. 2 251 373 A to Wu, U.S. Pat. No. 2,732,576 to Rosen, and French Patent No. 2,579,874 A to Pichon.

These types of brushes are useful for travelling, when only a single use is necessary. They are also useful by hotels as a gift for guests, and for other establishments, such as health clubs, hospitals and other places where the patrons may desire to brush their teeth.

While these devices serve a useful purpose, they lack several important features. First, once, the handle is inserted into the head, the toothpaste is released onto the bristles. A more preferable way of assembling the brush would be to have a first intermediate position where the handle is inserted into the head without releasing the toothpaste. Second, the above-described brushes do not have the capability of providing dental floss. These two features would significantly enhance the value and usefulness of disposable toothbrushes.

SUMMARY OF THE INVENTION

It is therefore an object of the present invention to overcome the drawbacks of the prior art and to provide a disposable toothbrush which is simple in design, compact and contains toothpaste.

It is another object of the present invention to provide a disposable toothbrush that can be assembled without ejecting the toothpaste.

It is further an object of the present invention to provide a disposable toothbrush wherein the handle is capable of holding a length of dental floss.

These and other objects of the invention are achieved by creating a disposable toothbrush having a handle and a head. The handle has a first section, a second section connected to and angled up from the first section, and a third section connected to the second section, wherein the third section has a lip on its free end.

The free end of the first section is bent to create an open cavity. A length of dental floss is stretched over the cavity and secured at each end. The user can then floss his or her teeth without touching the dental floss with their hands. The floss can be over any side of the toothbrush handle, i.e., front, back or sides.

The toothbrush head comprises a base with a substantially rectangular cross section having an open end and a closed end. The base is formed by a top side, a bottom side, a left side and, a right side. Each side on the base has both an inside face and an outside face, the inside faces forming a cavity within the base. The base has at least one ridge extending across at least one of the top side and bottom side on their inside surfaces near the open end.

The head also has a substantially rectangular middle plate having a width and a height. The height is bounded by a top face and a bottom face, with the bottom face attached to the top side of the base. The plate has a bore hole extending from the bottom face to the top face.

On the middle plate at the first end, is a thumbstop having a triangular cross section and extending longitudinally across the width of the middle plate.

On top of the middle plate is a substantially rectangular bristle plate having a top face and a bottom face. The bristle plate has a channel formed by a bore hole in communication with the middle plate channel. The bore hole is covered with a plastic sheet that may have perforations, to keep the toothpaste within the cavity fresh.

On the top face of the bristle plate are bristles which substantially cover the bristle plate. The bristles may be nylon or plastic. Therefore, when the thumbstop is pulled down, the top end of the handle slides into the cavity on the base and engages the ridge on the top or bottom side of the base. The toothbrush is thus assembled but with no chance of leakage of the toothpaste. When the user is ready for brushing, the handle is inserted further within the base, so that toothpaste located within the cavity is displaced out of the base, up through the middle plate, breaking the plastic sheet, and up through the bristle plate, wherein the toothpaste is then displaced onto the bristles.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views.

DETAILED DESCRIPTION OF THE PREFERRED EMBODIMENT

Figure 1:
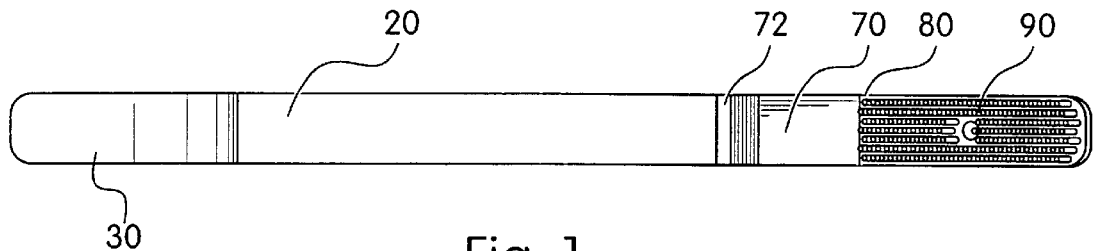
FIG. 1 is a top view representation of the disposable toothbrush according to the invention.

Referring now in detail to the drawings and, in particular, FIGS. 1–4, there is shown a disposable tooth brush 10 having an elongated handle 20. Handle 20 has three sections 22, 24 and 26.

Connected at an angle to first section 22, second section 24 has a height 24a and a width 24b. Second section 24 is connected in continuity with first section 22 and forms one piece therewith.

Third section 26 is connected in continuity with second section 24, forming one piece therewith. Third section 26 has a smaller height 26a and a smaller width 26b than second section 24. At an end of third section 26 is a lip 28, which extends up from third section 26. Lip 28 has a greater height than third section height 26a.

First section 22 has a bent portion 30, defining a cavity. A length of dental floss 35 is stretched across bent portion 30 and secured at each end. Floss 35 can be secured in any desired fashion, such as by threading it through holes in bent portion 30 and knotting it at either end, or by integrally molding floss 35 with the plastic of bent portion 30. Bent portion 30 can be molded in any desired shape, such as rounded, square, triangular, etc. There is a lip 38 on handle 22 to protect floss 35 from contact with the user's hand wile brushing.

As shown in FIGS. 5–8, tooth brush 10 also comprises an attachable head 40 which consists of a hollow base 50, a middle plate 70, a thumbstop 72, a bristle plate 80 and a set of bristles 90. Base 50 has a rectangular shaped cross section 52 at an open end 54 formed by a left side 56a, a right side 56b, a bottom side 58 and a top side 60. Opposite open end 54, base 50 has a closed end 62. Extending inside base 50 from open end 54, is a cavity 64 for holding toothpaste. This cavity extends substantially to the middle of base 50, and then turns up at a substantially perpendicular angle to an opening 66 on top face 60 of base 50. Cavity 64 is provided with a ridge 75 extending across inside top face 60 near open end 54. Ridge 75 acts as a stop for handle 20 when it is inserted into base 50 to assemble the toothbrush.

Middle plate 70 connects to top side 60 of base 50 and extends substantially parallel therewith, extending out of base 50 to thumbstop 72. Middle plate 70 has a hole 74 and is arranged on top face 60 such that hole 74 is in communication with opening 66 on base 50.

Bristle plate 80 has a front side 82 and a back side 84. Back side 84 connects to middle plate 70. Extending substantially perpendicular from front side 82 is a set of elongated bristles 90. This set of elongated bristles 90 substantially covers front side 82 of bristle plate 80. At the center of bristle plate 80 is a hole 86 which extends through bristle plate 80 to opening 66 on base 50.

The disposable tooth brush has handle 20, which fits snugly inside cavity 64 on base 50. To use toothbrush 10, one pulls down on thumbstop 72 pulling head 40 towards handle 20 and driving third section 26, lead by lip 28, into cavity 64. Third section 26 is temporarily stopped by lip 28 coming into contact with ridge 75 in head 50. Lip 28 and ridge 75 could also be located on the underside of the toothbrush as well. At this point, the toothbrush is assembled but the toothpaste is still sealed within cavity 64. When the user is ready for brushing, thumbstop 72 is pulled farther back so that third section 26 is driven entirely into cavity 64. This motion simultaneously drives toothpaste through cavity 64, up through opening 66, through hole 74 on middle plate 70 and hole 86 on bristle plate 80. When third section 26 substantially fills cavity 64, lip 28 comes into contact with stopper 68 on base 50. At this point substantially all the toothpaste is discharged from cavity 64 and injected between bristles 90 on front face 82.

In another embodiment of the invention, the open end of cavity 64 is closed by a plastic sheet 95. Plastic sheet 95 seals the toothpaste inside cavity 64 until toothbrush 10 is assembled. Plastic sheet 95 is easily punctured by handle 20 being inserted into cavity 64 of head 50.

Figure 2:
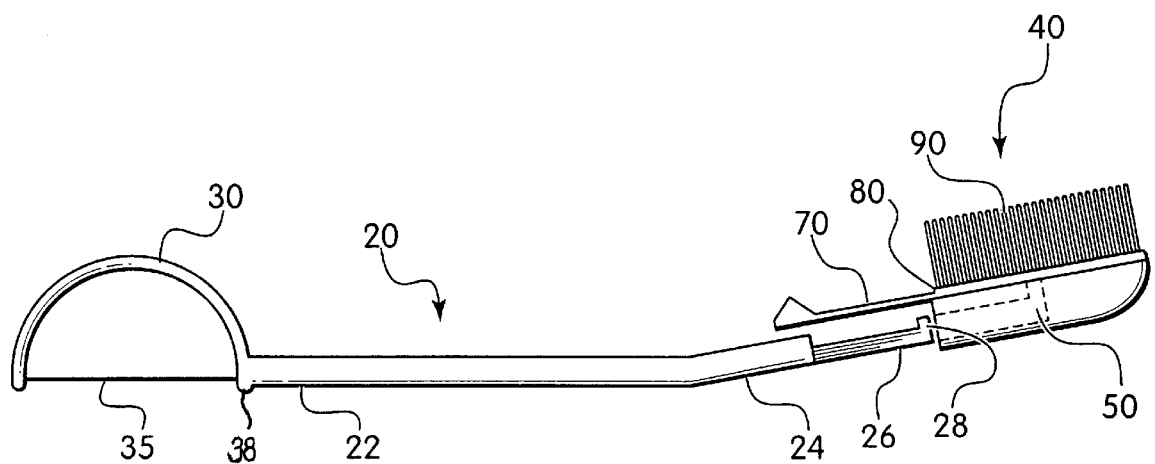
FIG. 2 is a lateral side view of the disposable tooth brush of FIG. 1.
Figure 3:
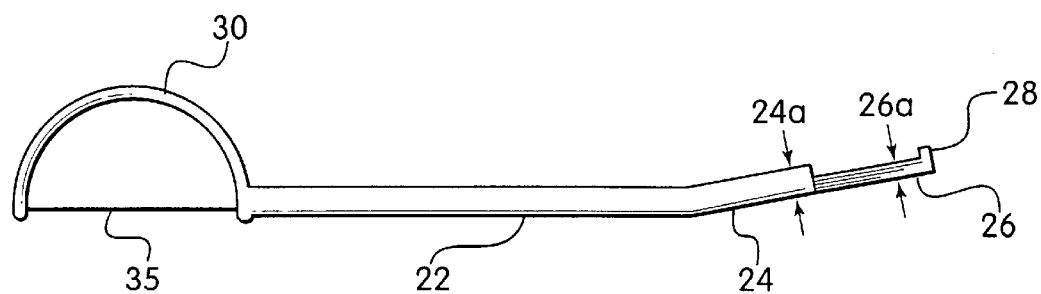
FIG. 3 is a lateral view of the tooth brush handle.
Figure 4:
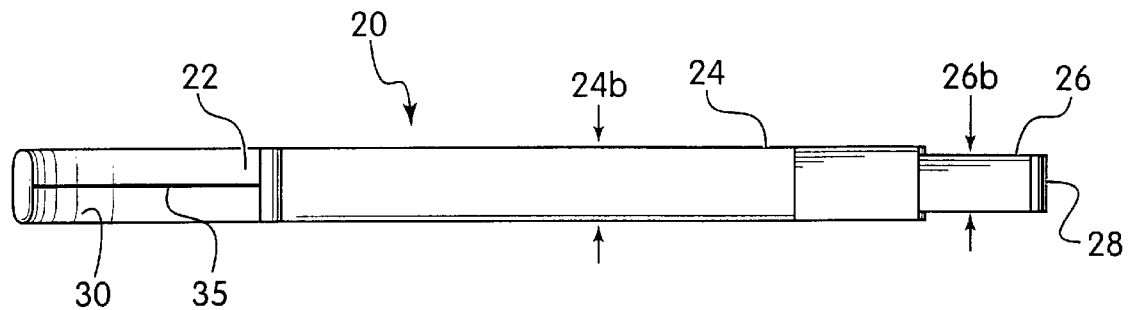
FIG. 4 is a top end view of the tooth brush handle.
Figure 5:
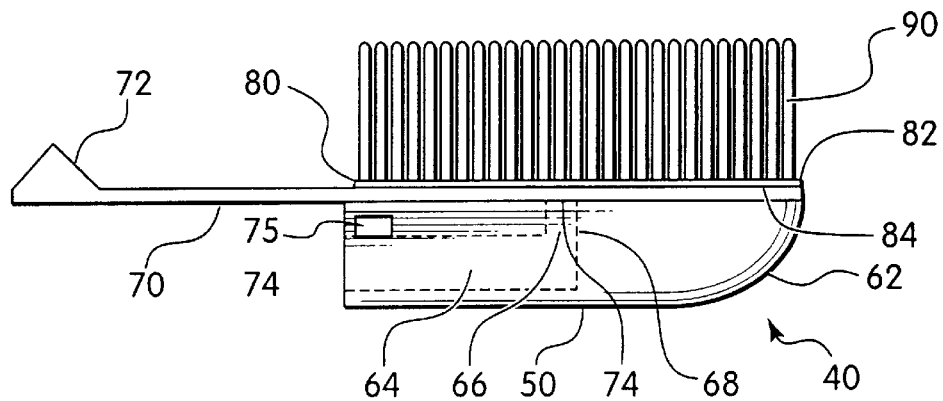
FIG. 5 is an enlarged view of the toothbrush head.
Figure 6:
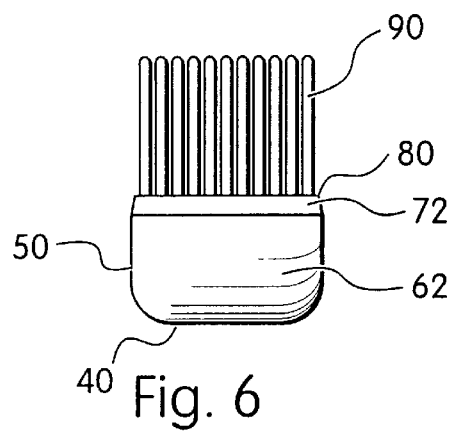
FIG. 6 is a top end view of the tooth brush head.
Figure 7:
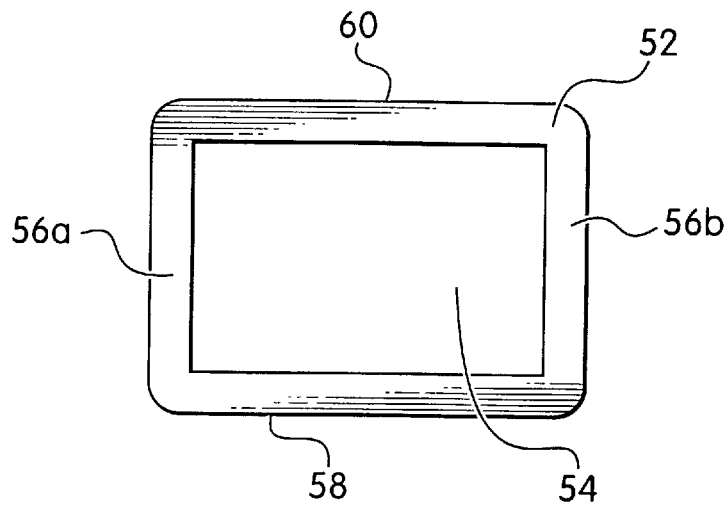
FIG. 7 is an open end view of the tooth brush base.
Figure 8:
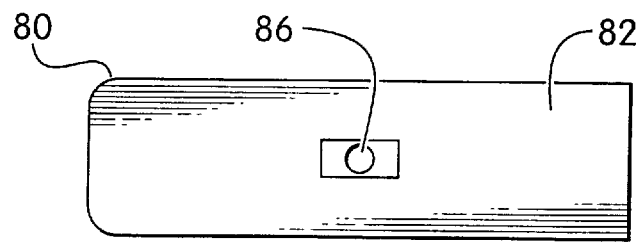
FIG. 8 is a top side view of the bristle plate.
Figure 9:
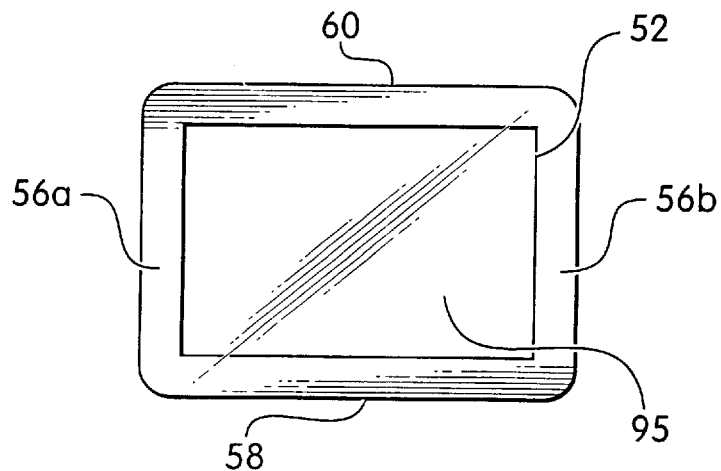
FIG. 9 is the second embodiment of the toothbrush head having a plastic shield over the open end of the tooth brush base.
Figure 10:
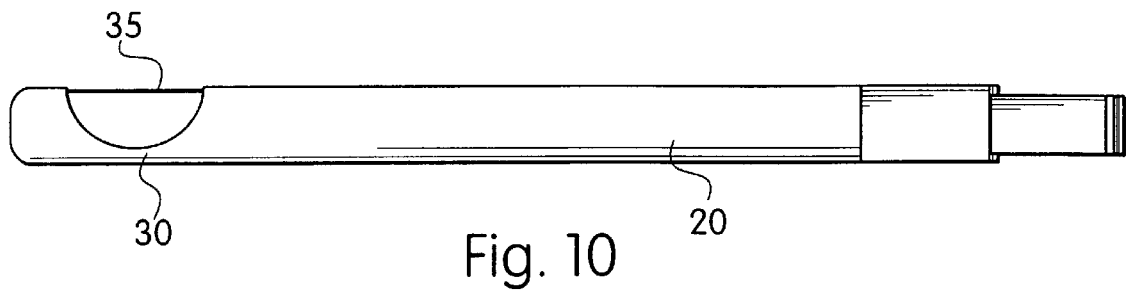
FIG. 10 is a bottom view of an alternative embodiment of the handle according to the invention.
Figure 11:
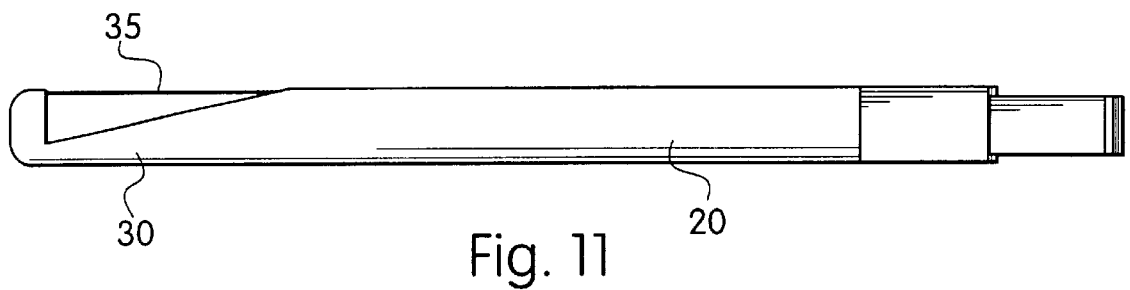
FIG. 11 is a bottom view of another alternative embodiment of the handle according to the invention.
Figure 12:
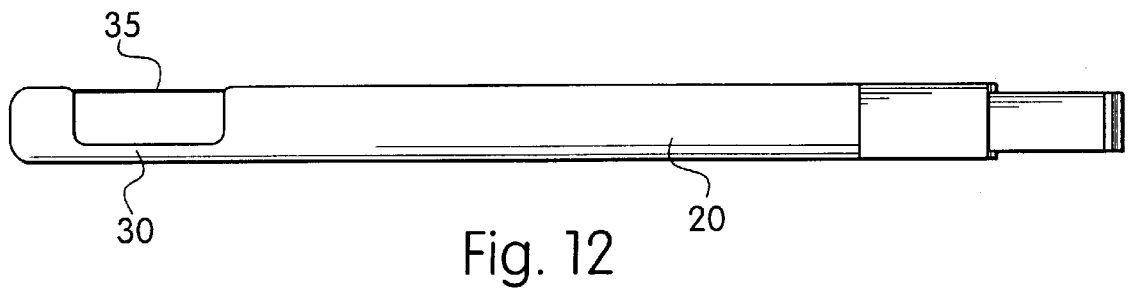
FIG. 12 is a bottom view of yet another alternative embodiment of the handle according to the invention.

FIGS. 10–12 shows different embodiments of handle 20, in which curved section 30 can take on various shapes, such as a round cutout, as shown in FIG. 10, a triangular cutout, as shown in FIG. 11, and a square cutout, as shown in FIG. 12. In addition, floss 35 can be positioned at any desired orientation with respect to handle 20. For example, floss 35 can be positioned on the rear as shown in FIGS. 1–3, one side, as shown in FIGS. 10–12, or on the top (not shown). All that is required is for the handle to be shaped in such a way that floss could be stretched across two points of the handle. The embodiments shown in the drawings enable the user to floss his or her teeth without touching the floss with their hands. This arrangement is thus more sanitary and easier to use than a loose length of floss.

Accordingly, while only a few embodiments of the present invention have been shown and described, it is obvious that many changes and modifications may be made thereunto without departing from the spirit and scope of the invention.

What is claimed is:

1. A disposable toothbrush comprising:

a handle having a first section, a second section connected to said first section and angled up from said first section, a third section connected to said second section wherein said third section has a lip on its free end;

means for mounting a length of dental floss on said handle such that said length of dental floss is stretched taut;

a base with a substantially rectangular cross section having an open and a closed end, said base formed by a top side, a bottom side, a left side and, a right side, each side having both an inside face and an outside face, said inside faces forming a cavity within said base;

at least one ridge formed on one of said top side and bottom side on their inside surfaces near the open end;

a substantially rectangular middle plate having a width and a height, with the height bounded by a top face and a bottom face, said bottom face attached to the top side of said base wherein said plate has a bore hole extending from said bottom face to said top face;

a thumbstop attached to the top face of said middle plate at a first end;

a substantially rectangular bristle plate having a top face and a bottom face, said bottom face attached to said top face of said middle plate, said bristle plate having a channel formed by a bore hole in communication with said middle plate bore hole and extending from said bottom face to said top face;

bristles extending up from and substantially covering said top face of said bristle plate, wherein pulling said thumbstop down causes the top end of said handle to slide into the cavity on said base and engage said ridge to assemble the toothbrush, and wherein further pulling on the thumbstop causes toothpaste located within said cavity to be displaced out of said base, up through said middle plate and up through said bristle plate wherein said toothpaste is then displaced onto said bristles.

2. The disposable toothbrush according to claim 1, wherein said base has a sloped top end.

3. The disposable toothbrush according to claim 1, wherein the cavity in said base is closed at a top end by a stopper.

4. The disposable toothbrush according to claim 1, wherein the third section on the handle has a smaller width and a smaller height than said second section.

5. The disposable toothbrush according to claim 1, wherein said second section on said handle is angled up by 10 degrees from said first section.

6. The disposable toothbrush according to claim 1, wherein said base is closed at the open end by a strip of plastic.

7. The disposable toothbrush according to claim 1, wherein said thumbstop has a triangular cross section and extends longitudinally across the width of said middle plate.

8. The disposable toothbrush according to claim 7, wherein the bent section is rounded.

9. The disposable toothbrush according to claim 7, wherein the bent section is rectangular.

10. The disposable toothbrush according to claim 1, wherein the means for mounting a length of dental floss on said handle comprises a bent section integrally formed with said handle and defining a cavity, said bent section having two ends, such that dental floss can be mounted between said two ends and a user can floss their teeth without touching the dental floss.

11. The disposable toothbrush according to claim 10, wherein the floss is fed through holes in said two ends of said bent section and secured outside said bent section.

12. The disposable toothbrush according to claim 10, wherein the floss is integrally molded with said bent section.

* * * * *